(12) United States Patent
Zhou et al.

(10) Patent No.: US 10,865,415 B2
(45) Date of Patent: Dec. 15, 2020

(54) PREVENTION, DIAGNOSIS AND TREATMENT OF CANCER OVEREXPRESSING GPR160

(71) Applicant: Shanghai Institute of Materia Medica, Chinese Academy of Sciences, Shanghai (CN)

(72) Inventors: Caihong Zhou, Shanghai (CN); Xinchuan Dai, Shanghai (CN); Mingwei Wang, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 11 days.

(21) Appl. No.: 15/765,163

(22) PCT Filed: Sep. 29, 2016

(86) PCT No.: PCT/CN2016/100879
§ 371 (c)(1),
(2) Date: Mar. 30, 2018

(87) PCT Pub. No.: WO2017/054759
PCT Pub. Date: Apr. 6, 2017

(65) Prior Publication Data
US 2019/0055565 A1  Feb. 21, 2019

(30) Foreign Application Priority Data
Sep. 30, 2015 (CN) .......................... 2015 1 0644076

(51) Int. Cl.
| C07H 21/04 | (2006.01) |
| C12N 15/113 | (2010.01) |
| A61K 48/00 | (2006.01) |
| A61K 31/713 | (2006.01) |
| C12N 15/11 | (2006.01) |
| A61P 35/00 | (2006.01) |

(52) U.S. Cl.
CPC ........ *C12N 15/1138* (2013.01); *A61K 31/713* (2013.01); *A61K 48/00* (2013.01); *A61P 35/00* (2018.01); *C12N 15/11* (2013.01); *C12N 15/113* (2013.01); *C12N 2310/14* (2013.01)

(58) Field of Classification Search
None
See application file for complete search history.

(56) References Cited

U.S. PATENT DOCUMENTS

2005/0246794 A1*  11/2005  Khvorova ............ A61K 31/713
                                                    800/286
2018/0201938 A1*   7/2018  Salvemini ............ C07K 14/705

FOREIGN PATENT DOCUMENTS

CN           101437536 A       5/2009

OTHER PUBLICATIONS

Qin, Y., et al. ("Quantitative expression profiling of G-protein-coupled receptors (GPCRs) in metastatic melanoma: the constitutively active orphan GPCR GPR18 as novel drug target." Pigment cell & melanoma research 24.1 (2011): 207-218).*
Rantala et al., A cell spot micro array method for production of high density siRNA transfection microarrays. BMC Genomics. Mar. 28, 2011;12:162. doi: 10.1186/1471-2164-12-162.
Zhou et al., G protein-coupled receptor GPR160 is associated with apoptosis and cell cycle arrest of prostate cancer cells. Oncotarget. Mar. 15, 2016;7(11):12823-39. doi: 10.18632/oncotarget.7313.
PCT/CN2016/100879, dated Dec. 14, 2016, International Search Report and Written Opinion.
PCT/CN2016/100879, dated Apr. 12, 2018, International Preliminary Report on Patentability.

* cited by examiner

Primary Examiner — Kimberly Chong
(74) Attorney, Agent, or Firm — Wolf, Greenfield & Sacks, P.C.

(57) ABSTRACT

Provided are a dsRNA construct of an orphan G-protein-coupled receptor GPR160 gene related to prostate cancer and the use thereof, wherein the dsRNA construct of the GPR160 gene and a composition thereof can prevent or treat prostate cancer.

14 Claims, 3 Drawing Sheets
Specification includes a Sequence Listing.

PREVENTION, DIAGNOSIS AND TREATMENT OF CANCER OVEREXPRESSING GPR160

RELATED APPLICATIONS

This application is a national stage filing under 35 U.S.C. 371 of International Patent Application Serial No. PCT/CN2016/100879, filed Sep. 29, 2016, entitled "PREVENTION, DIAGNOSIS AND TREATMENT OF CANCER OVEREXPRESSING GPR160," which claims priority to Chinese patent application number 201510644076.2, filed Sep. 30, 2015, the entire disclosure of each of which is incorporated by reference herein in its entirety.

TECHNICAL FIELD

The present invention belongs to the field of biotechnology. In particular, the present invention relates to the function of GPR160 gene associated with prostate cancer (PCa) and uses thereof, including inhibitors of GPR160 gene expression or antagonists for protein products thereof. The present invention also relates to diagnosis, prevention and treatment methods for PCa. The present invention relates to GPR160 gene and protein products thereof.

BACKGROUND

Prostate cancer is a kind of serious male age-related disease, which is one of the leading causes in man died of cancer in Europe and US. The incidence increases with age. Cancer lesions are found in more than half of older men over the age of 80 in prostate examination. Although the incidence of PCa in China is lower than that in Europe and US, it shows a remarkable growth trend and the ages of patient appears younger tendency in recent years. The studies and clinical treatments about the benign prostatic hyperplasia and etiology of PCa have received widespread attention in medical community around the world.

Traditional treatments for PCa include androgenic deprivation, prostatectomy, hormone replacement and radiotherapy/chemotherapy. Androgenic deprivation is commonly used for early PCa. Hormone replacement therapy is relatively simple and less painful, but easily leads to drug resistance. Surgical excision combined with radiotherapy and chemotherapy is commonly used for local PCa, however, patients often suffer from side effects such as hair loss or immune dysfunction. It has brought great troubles to the treatment due to the heterogeneity of the tumor and development from hormone-dependent to hormone-independent for most of PCa. Therefore, there is a broad market demand for the discovery of new therapeutic targets and the development of anti-PCa drugs.

A gene product, expression of which is up-regulated, in cancer tissues can be used as a potential anti-cancer drug target. At present, new drugs have been successfully developed based on molecular targets that are abnormally expressed in certain types of cancers and result in the proliferation and spread of cancer cells, such as Glivec for treating chronic myeloid leukemia and Herceptin for breast cancer, etc. A variety of over-expressed molecules have also been found in PCa and these molecules are classified as PCa markers or therapeutic targets. Exploration in this area is increasing.

In summary, there is an urgent need in the art to find genes or products thereof that are closely associated with the onset and progression of PCa and only specifically expressed in PCa tissue as intervention targets, thereby providing new ways for diagnosis, prevention and treatment for PCa.

SUMMARY OF THE INVENTION

The object of the present invention is to provide an inhibitor that effectively inhibits GPR160 gene expression.

In the first aspect of the present invention, a dsRNA construct is provided, wherein said dsRNA construct is double-stranded and the forward or reverse chain thereof has the structure shown in Formula I:

$$Seq_{Forward}\text{-}X\text{-}Seq_{Reverse} \qquad \text{Formula I}$$

wherein, $Seq_{forward}$ is GPR160 gene or a GPR160 gene fragment;

$Seq_{reverse}$ is a nucleotide sequence that is substantially complementary to $Seq_{forward}$;

X is a spacer sequence located between $Seq_{forward}$ and Sea and the spacer sequence is not complementary to $Seq_{forward}$ or $Seq_{reverse}$.

In another preferred embodiment, the sequence of GPR160 gene is shown in SEQ ID NO.: 1.

In another preferred embodiment, the sequence of GPR160 gene fragment is shown in SEQ ID NO.: 6 or 7.

In another preferred embodiment, the sequence of $Seq_{forward}$ is shown in SEQ ID NO.: 6 or SEQ ID NO.: 7.

In another preferred embodiment, the spacer sequence X is 1-100 bp in length, preferably 4-10 bp.

In another preferred embodiment, the GPR160 gene or GPR160 gene fragment is derived from mammal, preferably from human.

In another preferred embodiment, the dsRNA construct forms dsRNA shown as Formula II in the host cell:

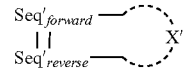

Formula II

Wherein, $Seq'_{forward}$ is a RNA sequence or a sequence fragment corresponding to the $Seq_{forward}$ sequence;

$Seq'_{reverse}$ is a sequence that is substantially complementary to $Seq'_{forward}$;

X' is none, or a spacer sequence located between $Seq'_{forward}$ and $Seq'_{reverse}$, and the spacer sequence is not complementary to $Seq'_{forward}$ and $Seq'_{reverse}$;

ll represents a hydrogen bond formed between $Seq'_{forward}$ and $Seq'_{reverse}$.

In the second aspect of the present invention, a dsRNA is provided with the structure shown in Formula II:

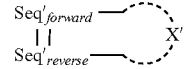

Formula II wherein, $Seq'_{forward}$ is a RNA sequence or a sequence fragment corresponding to the nucleotide sequence of a GPR160 gene or GPR160 gene fragment;

$Seq'_{reverse}$ is a sequence that is substantially complementary to $Seq'_{forward}$;

X' is none; or a spacer sequence located between Seq'$_{forward}$ and Seq'$_{reverse}$, and the spacer sequence is not complementary to Seq'$_{forward}$ and Seq'$_{reverse}$;

ll represents a hydrogen bond formed between Seq'$_{forward}$ and Seq'$_{reverse}$.

In another preferred embodiment, the sequence of GPR160 gene is shown in SEQ ID NO.: 1.

In another preferred embodiment, the sequence of GPR160 gene fragment is shown in SEQ ID NO.: 6 or SEQ ID NO.: 7.

In another preferred embodiment, the spacer sequence X is 1-100 bp in length, preferably 4-10 bp.

In another preferred embodiment, the GPR160 gene or GPR160 gene fragment is derived from mammal, preferably from human.

In the third aspect of the present invention, an expression vector is provided, wherein the expression vector comprises the construct according to the first aspect of the invention.

In another preferred embodiment, the expression vector is a viral vector or a plasmid vector.

In another preferred embodiment, the viral vector is a lentiviral vector and adenoviral vector.

In the fourth aspect of the present invention, a host cell is provided, wherein the host cell comprises the expression vector of the third aspect of the present invention or has a DNA sequence corresponding to the dsRNA construct described in the first aspect of the invention incorporated into it's chromosome.

In another preferred embodiment, a DNA sequence corresponding to the dsRNA construct of claim 1 is integrated into said host cell.

In the fifth aspect of the present invention, a composition is provided, wherein the composition contains an inhibitor or antagonist inhibiting GPR160 gene expression or antagonizing GPR160 receptor activity; and preferably, the inhibitor includes: Small interfering molecules or antisense nucleotides that specifically interfere with GPR160 gene expression; or a biological or chemical ligand that specifically binds to a GPR160 gene-encoded protein.

In another preferred embodiment, the composition contains the dsRNA construct according to the first aspect of the present invention and/or the dsRNA according to the second aspect of the present invention, and a pharmaceutically acceptable carrier.

In another preferred embodiment, the composition is a composition for inhibiting the expression of endogenous GPR160 gene in an animal.

In another preferred embodiment, the dsRNA has a sequence corresponding to SEQ ID NO.: 6 or SEQ ID NO.: 7.

In another preferred embodiment, the composition is a reagent or a pharmaceutical composition.

In the sixth aspect of the present invention, use of the dsRNA construct according to the first aspect of the invention, or the dsRNA according to the second aspect of the invention, or the expression vector according to the third aspect of the invention, or the composition according to the fifth aspect of the invention is provided for preparing an inhibitor for inhibiting GPR160 gene expression.

In another preferred embodiment, the GPR160 gene is a human GPR160 gene. In another preferred embodiment, the use also includes preparation of a drug for the prevention or treatment of cancer.

In another preferred embodiment, the cancer includes, but is not limited to: a solid tumor such as prostate cancer, nasopharyngeal cancer, breast cancer, lung cancer, gastric cancer, liver cancer, pancreatic cancer, colorectal cancer; a blood tumor such as leukemia, lymphoma; a skin tumor such as melanoma, etc.

In the seventh aspect of the present invention, a method for preparing dsRNA is provided, including steps of:

(i) preparing a construct expressing dsRNA, wherein the construct is double-stranded and its sense or antisense strand contains the structure shown in Formula 1:

$$Seq_{Forward}\text{-}X\text{-}Seq_{Reverse} \qquad \text{Formula I}$$

wherein,

Seq$_{forward}$ is a GPR160 gene or GPR160 gene fragment;

Seq$_{reverse}$ is a nucleotide sequence that is substantially complementary to Seq$_{forward}$;

X is a spacer sequence located between Seq$_{forward}$ and Seq$_{reverse}$, and the spacer sequence is not complementary to Seq$_{forward}$ or Seq$_{reverse}$;

(ii) transferring the construct in step (i) into a host cell, thereby forming dsDNA as shown in Formula II in the host cell through expression,

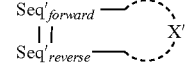

Formula II wherein,

Seq'$_{forward}$ is a RNA sequence or sequence fragment corresponding to Seq$_{forward}$;

Seq'$_{reverse}$ is a sequence that is substantially complementary to Seq'$_{forward}$;

X' is none, or a spacer sequence located between Seq'$_{forward}$ and Seq'$_{reverse}$, and the spacer sequence is not complementary to Seq'$_{forward}$ or Seq'$_{reverse}$;

ll represents a hydrogen bond formed between Seq'$_{forward}$ and Seq'$_{reverse}$.

In another preferred embodiment, the GPR160 gene sequence is shown in SEQ ID NO.: 1.

In another preferred embodiment, the GPR160 gene fragment sequence is shown as SEQ ID NO.: 6 or SEQ ID NO.: 7.

In another preferred embodiment, the spacer sequence X is 1-100 bp in length, preferably 4-10 bp.

In another preferred embodiment, the GPR160 gene or GPR160 gene fragment is derived from mammal, preferably from human.

In the eighth aspect of the present invention, a use of a nucleic acid sequence is provided for preparing an inhibitor for GPR160 gene expression, wherein the nucleotide sequence is shown in SEQ ID NO.: 6 or SEQ ID NO.: 7.

In another preferred embodiment, the inhibitor for expression is siRNA.

Other aspects of the present invention will be apparent to those skilled in the art from the disclosure herein.

It should be understood that in the present invention, any of the technical features specifically described above and below (such as in the Examples) can be combined with each other, thereby constituting new or preferred technical solutions that are not described one by one in the specification.

DETAILED DESCRIPTION

Figure 1:
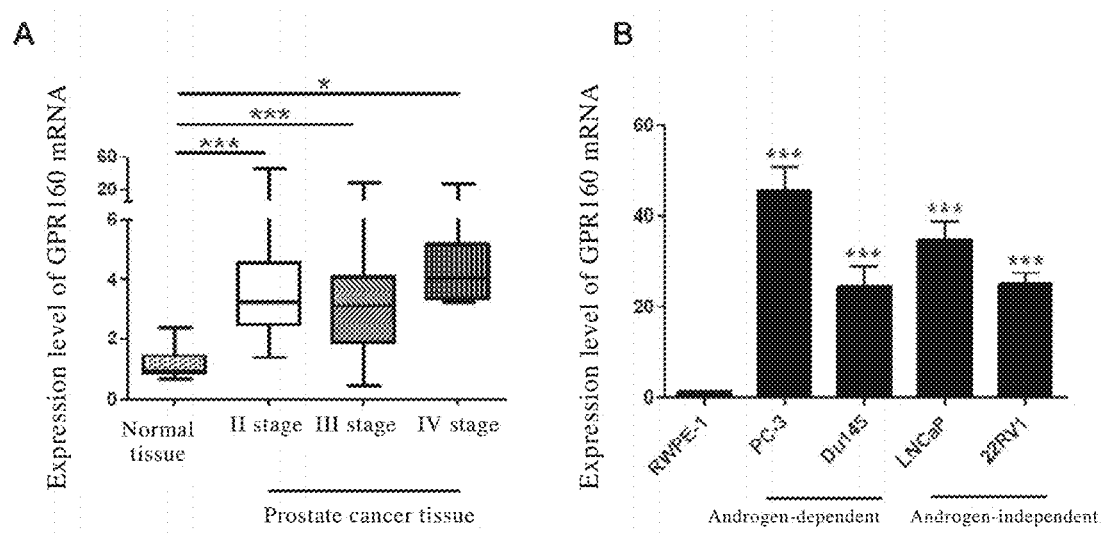
FIG. 1 shows the expression of GPR160 in human prostate cancer tissues and prostate cancer cell lines. A shows the expression of GPR160 in normal prostate and prostate cancer tissues; B shows the expression of GPR160 in normal prostate epithelial cells and four prostate cancer cell lines (PC-3, DU145, LNCaP and 22RV1).

The siRNAs that can effectively inhibit the GPR160 gene was obtained by the inventor through extensive and in-depth research. The experimental results show that the siRNAs can significantly inhibit the growth of tumors, and based on this, the present invention has been completed.

Before describing the present invention, it should be understood that the present invention is not limited to the specific methods and experimental conditions described as the methods and conditions can change. It should also be understood that the terms used herein are for the purpose of describing a specific embodiment only, and are not intended to be limiting. The scope of the invention will only be limited by the appended claims.

Unless otherwise defined, all technical and scientific terms used herein have the same meaning as commonly understood by one of ordinary skill in the art to which this invention belongs. As used herein, the term "about", when used in reference to a specifically recited number, means that the value can vary by no more than 1% from the recited value. For example, as used herein, the expression "about 100" includes 99 and 101 and all values between 99 and 101 (for example, 99.1, 99.2, 99.3, 99.4, etc.).

Although any methods and materials similar or equivalent to those described herein can be used in the practice or test of the present invention, the preferred methods and materials are exemplified herein.

The present invention discloses that GPR160 gene is highly expressed in PCa tissues and cells, and is closely related to the occurrence and development of PCa. Inhibition of over-expression of GPR160 can inhibit tumor cell growth and induce apoptosis, suggesting that GPR160 can be used as a target for PCa intervention.

One object of the present invention is to provide a G protein-coupled receptor GPR160 gene associated with PCa and uses thereof.

Another object of the present invention is to provide uses of GPR160 in clinical diagnosis, therapeutic evaluation and prognosis of PCa.

Another object of the present invention is to provide an inhibitor of GPR160 gene expression or receptor antagonist and uses thereof in preparation of a medicament for preventing or treating PCa.

Another object of the present invention is to provide a method for preventing or treating PCa by using the inhibitor of GPR160 gene expression or receptor antagonist.

Another object of the present invention is to provide a method for screening active substances for preventing or treating PCa based on the GPR160 as a target for drug action.

In a preferred embodiment of the invention, the present invention provides a method for diagnosis, efficacy evaluation and prognosis estimation of PCa based on GPR160 gene or a protein product, GPR160 receptor thereof.

In a preferred embodiment, the method includes detecting the level of expression of the GPR160 gene using substances that specifically recognize GPR160 gene or encoded proteins thereof (including: primers that specifically amplify GPR160 gene; probes that specifically recognize GPR160 gene; or ligands that specifically bind to GPR160 protein).

In a preferred embodiment, the method includes, but is not limited to, PCR, NGS, ELISA, Western Blot, isotope labeling, flow cytometry, etc.

In a preferred embodiment, the object to be detected by the method is human body samples, including but not limited to blood, cells, tissues and body fluids.

In a preferred embodiment, the primers used in the PCR detection method include the corresponding sequence:
the nucleotide sequence as shown in SEQ ID NO.: 2; and/or
the nucleotide sequence as shown in SEQ ID NO.: 3.

In a preferred embodiment of the invention, the present invention provides uses of an inhibitor that inhibits GPR160 gene expression or antagonizes GPR160 receptor activity, for the preparation of a composition for preventing or treating prostate cancer (PCa).

In a preferred embodiment, the PCa tissue or cell expresses GPR160.

In a preferred embodiment, the inhibitor is selected from (but not limited to):
small interfering molecule or antisense nucleotide that specifically interferes with GPR160 gene expression; or
biological or chemical ligand that specifically binds to a protein encoded by the GPR160 gene.

In a preferred embodiment, the small interfering molecule is a small interfering RNA (siRNA).

In a preferred embodiment, the siRNA comprises a sense nucleotide and an antisense nucleotide of GPR160 gene.

In a preferred embodiment, the small interfering RNA molecule has a nucleotide sequence corresponding the sequence shown in SEQ ID NO.: 1 as a target sequence.

In a preferred embodiment, the siRNA molecule contains the corresponding sequence:
the nucleotide sequence as shown in SEQ ID NO.: 6; and/or
the nucleotide sequence as shown in SEQ ID NO.: 7.

In a preferred embodiment, the GPR160 gene is derived from mammal, preferably human.

In a preferred embodiment of the invention, the present invention provides a method for prevention or treatment of PCa, including administering a siRNA composition to a subject in need thereof, and the composition contains a nucleotide sequence that reduces GPR160 gene expression.

In a preferred embodiment, the method includes administering antisense composition to a patient, and the composition contains a nucleotide sequence that is complementary to the GPR160 encoding sequence.

In a preferred embodiment, the method includes administering effective amount of an antagonist to patients, and the antagonist binds to a receptor encoded by GPR160 gene.

In a preferred embodiment of the invention, the present invention provides a siRNA molecule for preventing or treating PCa, and the siRNA is a double-stranded molecule, which comprises a sense strand and an antisense strand, wherein the sense strand includes the corresponding sequence:

the nucleotide sequence as shown in SEQ ID NO.: 6; and/or the nucleotide sequence as shown in SEQ ID NO.: 7.

The antisense strand contains ribonucleotide sequence complementary to the sense strand, and the sense strand and the antisense strand hybridize to each other to form the double-stranded molecule.

Preferably, when the double-stranded molecule is introduced into a cell expressing GPR160 gene, the expression of the gene is inhibited.

In another preferred embodiment, the target sequence of the double-stranded molecule comprises at least about 10 contiguous nucleotides of nucleotide sequence as shown in SEQ ID NO.: 1.

Preferably, the target sequence of the double-stranded molecule comprises at least about 19 to 25 contiguous nucleotides of nucleotide sequence as shown in SEQ ID NO.: 1.

Preferably, the double-stranded molecule is a single ribonucleotide transcript consisting of a sense strand and an antisense strand.

In a preferred embodiment of the invention, the present invention provides a composition for preventing or treating PCa, wherein the composition contains:

1. Effective amount of an inhibitor of GPR160 gene expression or receptor antagonist;
2. A pharmaceutically acceptable carrier.

Preferably, the composition contains siRNA molecules of GPR160 gene.

Preferably, the siRNA is a double-stranded molecule, which comprises a sense strand and an antisense strand, wherein the sense strand includes the corresponding sequence:

the nucleotide sequence as shown in SEQ ID NO.: 6; and/or the nucleotide sequence as shown in SEQ ID NO.: 7.

The antisense strand contains a ribonucleotide sequence that is complementary to the sense strand, wherein the sense strand and the antisense strand hybridize to each other to form the double stranded molecule.

Preferably, when the double-stranded molecule is introduced into a cell expressing GPR160 gene, the expression of the gene is inhibited.

In a preferred embodiment of the invention, the present invention provides a method for screening potential substances with preventing or treating activities on PCa, the method including:

1. treating a system expressing GPR160 using a tested substance;
2. Detecting GPR160 gene expression and activity in the system;
3. Selecting the tested substance that inhibits GPR160 gene expression or reduces its receptor activity.

In another preferred embodiment, step (1) of the method includes: in the test group, adding a tested substance to the system expressing GPR160, and/or step (2) of the method includes: detecting the expression or activity of GPR160 gene in the system treated by the tested substance and compared with the control, wherein the control was a GPR160 expression system without adding the tested substance.

If the GPR160 gene expression or receptor activity in the system containing the tested substance is statistically lower than that of the control (preferably significant lower than, for example, 20% or more lower, preferably 50% or more lower; more preferably 80% or more lower), suggesting that the tested substance has the potential for preventing or treating PCa.

In another preferred embodiment, the system is a cell.

In another preferred embodiment, the method also includes performing cell function and/or animal experiments on the obtained active substance to further select and determine whether it is beneficial for preventing or treating PCa.

In another preferred embodiment of the invention, the present invention provides a double-stranded molecule comprising a sense strand and an antisense strand, wherein the sense strand comprises a ribonucleotide corresponding to a target sequence consisting of SEQ ID NO.: 6 and/or SEQ ID NO.: 7, and the antisense strand contains a ribonucleotide sequence that is complementary to the sense strand, wherein the sense strand and the antisense strand hybridize to each other to form the double-stranded molecule, and wherein the double-stranded molecule is introduced into a cell expressing GPR160 gene to inhibit the expression of the gene.

In another preferred embodiment, the target sequence comprises at least about 10 contiguous nucleotides of nucleotide sequence as shown in SEQ ID NO.: 1.

In another preferred embodiment, the target sequence comprises at least about 19 to 25 contiguous nucleotides of nucleotide sequence as shown in SEQ ID NO.: 1.

In another preferred embodiment, the double-stranded molecule is single ribonucleotide transcript consisting of the sense and antisense strands.

In order to clarify the content of the invention and not be limited by it, the invention is divided into the following sections for detailed description.

A. Definition

Unless otherwise defined, the technical and scientific terms used herein have the same meaning as the general understanding of the general technology in the field to which the present invention belongs. All patent applications, and other publications and sequences from GenBank and other databases mentioned here are incorporated by reference. If the definitions described in this section are contrary to, or inconsistent with the definitions of other patent applications, patent and other publications cited in the present application, the definitions described in this section dominate.

Unless otherwise specified, the terms "a", "an", and "the" as used herein are intended to mean "at least one" or "one or more".

As used herein, "prostate cancer" refers to a common malignancy of the male reproductive system, which is predominantly adenocarcinoma.

As used herein, an "effective amount" of a compound used to treat a particular disease refers to a dose that is sufficient to improve or to some extent reduce the symptoms associated with the disease. The present invention mainly deals with the pathological up-regulation of gene expression. The "effective amount" varies depending on the size, number, or metastatic potential of the cancer spot in the individual. This dose can be administered as a single dose or as a treatment regimen. This dose can cure disease, but it is typically administered for relieving symptoms. When treatment is used for prevention, "effective" means delaying or preventing the formation of prostate cancer, or preventing, delaying, or alleviating clinical symptoms. Assessment of prostate tumors can be performed using standard clinical protocols. In addition, the effectiveness can be measured according to any known method for the diagnosis and treatment of PCa. For example, the diagnosis of PCa can be performed through the identification of symptoms of abnormal conditions, such as weight loss, abdominal pain, back pain, anorexia, nausea, vomiting, general malaise, weakness and yellow disease. Repeated administration may be necessary for improving symptoms.

As used herein, "treatment" refers to the improvement of disease and symptoms in any way, or other beneficial changes. Treatment also includes the application of the present invention in medicine.

As used herein, administration of a particular pharmaceutical composition for "improving" symptoms of a particular disease means that any reduction in symptom, whether permanent, temporary, prolonged, transient, can be attributed to or related to the administration of the pharmaceutical composition.

As used herein, "composition" refers to any mixture. The mixture can be a solution, suspension, liquid, powder, ointment, aqueous, non-aqueous or any combination thereof.

As used herein, "combination" refers to any combination of two or more.

The term "subject" as used herein includes humans and animals, such as dogs, cats, cows, pigs, rodents, etc. Experienced practitioners should understand that the subject is an individual suitable and willing to accept prevention and treatment.

B. GPR160 Gene

GPR160 belongs to Orphan G protein-coupled receptors. Human GPR160 gene is located on chromosome 3, q26.2-q27. The encoded protein belongs to the group A protein-coupled receptor and contains 338 amino acids. At present, the physiological functions of GPR160 remain unknown, much less the relationship with the occurrence and development of cancer. In the present invention, qRT-PCR detection was performed on cDNA chips of normal prostate and prostate cancer tissues, and the transcription level of GPR160 was found significantly higher in prostate cancer tissues than in normal prostate tissues. The present inventors also analyzed the expression of GPR160 in four PCa cells (PC-3, DU145, LNCaP, and 22RV1) and a normal prostate epithelial cell (RWPE-1). The expression level of GPR160 in PCa cell line was found to be significantly higher than that in the normal prostate epithelium. The above results suggest that the expression of GPR160 has a certain relationship with the occurrence and development of PCa.

In order to investigate whether intervention of GPR160 expression can inhibit the growth of PCa cells, the present inventors prepared a lentivirus containing siRNA molecules that can significantly reduce the level of endogenous GPR160 expression and efficiently infecting PCa cell lines. It was found that expression of most of the endogenous GPR160 in PCa cells treated with GPR160 siRNA molecules was reduced, cell growth was inhibited, and the number of formed clones was significantly reduced when compared with the control siRNA molecule treatment, suggesting that the growth of PCa cells can be inhibited by reducing the expression of GPR160.

Preferably, the GPR160 gene is human GPR160 gene, the polynucleotide sequence of which is shown as follows:

```
Human GPR160 gene (NM_014373.2),
                                                              SEQ ID NO.: 1
   1 ggcccggacg ggacgtgcgc gctcaaaggt tgcccgtctc tgacgcccgc atttcctggt 61 ctggagccgg ctgagccaca gcagggtcgc cgcggggtcc cggggccgtg ctcccctgcc 121 cctcccggga gcgcgcgggg cggggcgggg cggggcggga ccaggcgggc gagctgggcc 181 ctcgcccctc cctcgggcgg tcacctgggc acgggcgctg caggtgtcgg ggcctcaacc 241 ttgcggagcc gacagccatc gatcctcggg tggcctcgag gtggtggcag ggccgccccc 301 tgcagtccgg agacgaacgc acggaccggg cctccggagg caggttcggc tggaaggaac 361 cgctctcgct tcgtcctaca cttgcgcaaa tgtctccgag cttactcaca tagcatattg 421 gtatatcaaa atgaaatgca aggaaccaaa aataacataa ttgaaggcag taaaagtgaa 481 attaaatagg aagatcatca gtcaaggaag acccactgga gaggacagaa aatgaagcag 541 tgttttatca tgtgtatttc agcaggtctt cttgaaattt aactaaaaat atgactgctc 601 tctcttcaga gaactgctct tttcagtacc agttacgtca aacaaaccag cccctagatg 661 ttaactatct gctattcttg atcatacttg ggaaaatatt attaaatatc cttacactag 721 gaatgagaag aaaaaacacc tgtcaaaatt ttatggaata tttttgcatt tcactagcat 781 tcgttgatct tttacttttg gtaaacattt ccattatatt gtatttcagg gattttgtac 841 ttttaagcat taggttcact aaataccaca tctgcctatt tactcaaatt atttccttta 901 cttatggctt tttgcattat ccagtttttcc tgacagcttg tatagattat tgcctgaatt 961 tctctaaaac aaccaagctt tcatttaagt gtcaaaaatt attttatttc tttacagtaa
```

```
-continued
1021 ttttaatttg gatttcagtc cttgcttatg ttttgggaga cccagccatc taccaaagcc 1081 tgaaggcaca gaatgcttat tctcgtcact gtcctttcta tgtcagcatt cagagttact 1141 ggctgtcatt tttcatggtg atgattttat ttgtagcttt cataacctgt tgggaagaag 1201 ttactactttt ggtacaggct atcaggataa cttcctatat gaatgaaact atcttatatt 1261 ttccttttc atcccactcc agttatactg tgagatctaa aaaaatattc ttatccaagc 1321 tcattgtctg ttttctcagt acctggttac catttgtact acttcaggta atcattgttt 1381 tacttaaagt tcagattcca gcatatattg agatgaatat tccctggtta tactttgtca 1441 atagttttct cattgctaca gtgtattggt ttaattgtca caagcttaat ttaaaagaca 1501 ttggattacc tttggatcca tttgtcaact ggaagtgctg cttcattcca cttacaattc 1561 ctaatcttga gcaaattgaa aagcctatat caataatgat ttgttaatat tattaattaa 1621 aagttacagc tgtcataaga tcataatttt atgaacagaa agaactcagg acatattaaa 1681 aaataaactg aactaaaaca acttttgccc cctgactgat agcatttcag aatgtgtctt 1741 ttgaagggct atgataccag ttattaaata gtgttttatt ttaaaaacaa aataattcca 1801 agaagttttt atagttattc agggacacta tattacaaat attactttgt tattaacaca 1861 aaaagtgata agagttaaca tttggctata ctgatgtttg tgttactcaa aaaaactact 1921 ggatgcaaac tgttatgtaa atctgagatt tcactgacaa ctttaagata tcaacctaaa 1981 catttttatt aaatgttcaa atgaaagcaa gaaaaaaaaa a
```

C. Diagnostic Methods Based on GPR160 Gene or Protein Products Thereof

Based on the above findings, GPR160 can be used as a marker for diagnosing PCa for:
1. PCa typing, differential diagnosis and/or susceptibility analysis;
2. Assessment of PCa treatment response, drug efficacy, and prognosis in the relevant population and selection of the appropriate treatment plan.
3. Early assessment, early monitoring and early prevention of the risk of PCa in the relevant population. For example, people with abnormal expression of GPR160 were selected for targeted interventions.

Thus, use of a GPR160 gene or protein for the preparation of reagents and/or kits for diagnosing (and/or detecting) PCa, for the diagnosis, evaluation of therapeutic effects, and prognostic predictions of PCa is provided in the present invention.

The expression of GPR160 gene can be detected by various techniques known in the art. These methods are all included in the present invention including but not limited to PCR, NGS, ELISA, Western Blot, isotope labeling, flow cytometry, etc.

D. GPR160 Gene Inhibitor or Receptor Antagonist

Based on the above findings, the present invention provides uses of an inhibitor of GPR160 gene expression or receptor antagonist for the preparation of a composition for preventing or treating PCa.

As used herein, the GPR160 gene inhibitors or receptor antagonists include inhibitors, down-regulators, blockers, blockers, antagonists, etc.

The GPR160 gene inhibitor or receptor antagonist refers to any substance that can down-regulate GPR160 gene expression, decrease receptor activity, reduce GPR160 gene or receptor stability, and shorten the time of receptor action or inhibit gene transcription and translation. These substances can be used in the present invention as GPR160 gene inhibitors or receptor antagonists for the prevention or treatment of PCa. For example, the inhibitor is: a siRNA molecule or antisense nucleotide specifically interfering with GPR160 gene expression; and the antagonist is: a biological or chemical ligand specifically binding to the GPR160 receptor.

As a preferred embodiment of the present invention, the inhibitor is a siRNA molecule specific for GPR160 gene. As used herein, the term "small interfering RNA (siRNA)" refers to a short double-stranded RNA molecule that is capable of targeting a mRNA of an homologous complementary sequence, thereby degrading a specific mRNA. This process is RNA interference.

As a particularly preferred embodiment of the present invention, a siRNA molecule having good effects is provided. The siRNA molecules can specifically interfere with the expression of human GPR160 gene, and have no significant homology with other human nucleic acid sequences, and have been experimentally verified to have a good effect of interfering with GPR160 expression. The siRNA molecule comprises one or more of the sequences of SEQ ID NO: 6 and SEQ ID NO: 7. More preferably, the siRNA is a combination of siRNA molecules comprising the sequences of SEQ ID NO: 6 and SEQ ID NO: 7.

The method for preparing the siRNA of the present invention is not particularly limited, including but not limited to: chemical synthesis, in vitro transcription, and in vivo expression with specific vectors, etc. After a person skilled in the art knows the sequences of siRNAs provided in the present invention, the siRNAs can be conveniently prepared or expressed in various ways. For example, in a preferred embodiment of the present invention, the siRNA is chemically synthesized, while in another preferred embodiment, it is expressed using lentiviral expression vectors.

SiRNAs can be prepared as double-stranded nucleic acids, containing a sense strand and an antisense strand, which form a double strand only under hybridization conditions. A double-stranded RNA complex can be prepared from the sense and antisense strands separated from each other. For example, in chemical synthesis, the complementary sense and antisense strands are synthesized separately and can be hybridized by annealing to produce a synthetic double-stranded RNA complex. In addition, the sense and antisense strands contained in siRNA can be prepared by one or more expression cassettes encoding the sense and antisense strands. When the sense and antisense strands are encoded by a single expression cassette, they can be cleaved from the produced transcripts to form isolated sense and antisense strands, which then hybridize to produce double-stranded siRNAs. For example, a lentiviral expression system is used, and the sense and antisense strands form shRNAs via a linking sequence, which are constructed into known lentiviral expression vectors. After in vivo expressed, it becomes a siRNA molecule through enzymatic digestion, thereby further exerting the effect of specifically silencing the expression of endogenous GPR160 gene in PCa. In a preferred embodiment of the present invention, the sequence of the construct corresponding to the shRNA of the present invention consisting of a sense strand and an antisense strand via a linker sequence includes the sense strand sequence shown in SEQ ID NO.: 6 and the antisense strand sequence shown in SEQ ID NO.: 11:

```
                                        (SEQ ID NO.: 6)
5'-TTGGTACAGGCTATCAGGATAACTTCCTA-3'

(SEQ ID NO.: 11)
5'-TAGGAAGTTATCCTGATAGCCTGTACCAA-3'.
```

In a preferred embodiment of the present invention, the sequence of constructs corresponding to the shRNA of the present invention consisting of a sense strand and an antisense strand via linker sequences includes the sense strand sequence shown in SEQ ID NO.: 7 and the antisense strand sequence shown in SEQ ID NO.: 12:

```
                                        (SEQ ID NO.: 7)
5'-TTCTATGTCAGCATTCAGAGTTACTGGCT-3'

(SEQ ID NO.: 12)
5'-AGCCAGTAACTCTGAATGCTGACATAGAA-3'.
```

The siRNA molecules can be delivered into cells using a variety of techniques known in the art.

E. Drug Screening Technology Targeting GPR160

Based on the fact that GPR160 is over-expressed in PCa cells and interference with their expression can inhibit the growth of tumor cells, it can be used as a target for screening substances for inhibiting GPR160 gene expression or with antagonizing receptor activity, thereby providing new drugs for the prevention and treatment of PCa. Thus, the present invention provides a method for screening substances that inhibit the expression of GPR160 gene or antagonize receptor activity. The method includes:

1. treating the system expressing GPR160 by using a substance to be tested;
2. Detecting effects of the tested substance on GPR160 gene expression and activity in the system;
3. Selecting the tested substance that inhibits GPR160 gene expression or reduces its receptor activity.

The system is preferably a cell (or cell culture), and the cell may be cells that endogenously express GPR160 or recombinantly express GPR160. For example, the cells are selected from PC-3, LNCaP or engineered cell lines expressing GPR160 upon gene transfection, such as CHO, HEK293, etc.

In a preferred embodiment of the present invention, a control may also be provided in order to readily observe changes in GPR160 expression or receptor activity, and the control may be a GPR160 expression system without adding the tested substance.

As a preferred embodiment of the present invention, the method further comprises performing cell function and/or animal experiments on the obtained active substance to further select and determine whether it is beneficial for preventing or treating PCa.

F. GPR160 Gene Inhibitor or Receptor Antagonist Composition

The present invention also provides a composition for preventing or treating PCa, and the composition contains an effective amount of a GPR160 gene inhibitor or receptor antagonist and a pharmaceutically acceptable carrier. Any GPR160 gene inhibitors or receptor antagonists mentioned above can be used in the preparation of the composition.

As a preferred embodiment of the present invention, a composition for preventing or treating PCa is provided, and the composition contains effective amount of the GPR160-targeting siRNA molecule, the antibody or chemical antagonist that specifically binds the receptor, and the pharmaceutically acceptable carrier of the present invention.

As used herein, "effective amount" refers to a therapeutic amount that can be functional or active in humans and/or animals and can be accepted by humans and/or animals. The "pharmaceutically acceptable carrier" refers to a carrier that is administered in a therapeutic amount, including various excipients and diluents. The term refers to the agent carrier itself is not essential active ingredients and is not excessively toxic after administration. Suitable carriers are well-known to those skilled in the art and may contain liquids such as water, saline, buffers, and possibly auxiliary substances such as fillers, lubricants, flow aids, wetting agents or emulsifiers. pH buffer material, etc. The vector may also contain cell transfection reagent.

G. Treatment and Prevention Methods

The present invention relates to a method of preventing or treating PCa with high expression of GPR160 and its symptoms. The method includes administering an effective amount of an inhibitor that selectively interferes with GPR160 gene expression or an antagonist that reduces GPR160 receptor activity and combinations thereof to a subject in need thereof or willing to receive prophylaxis or treatment to prevent or treat the above mentioned disease or condition.

Preferably, the above prostate cancer is prevented or treated by administering an effective amount of a specific siRNA molecule of the present invention targeting GPR160, GPR160 receptor-specific biological or chemical antagonist, and a pharmaceutically acceptable carrier.

Any subject can be treated with this method, preferably mammals, more preferably human.

The GPR160 inhibitors or antagonists of the present invention may be used alone or in combination with other anti-neoplastic agents that have been marketed or will be marketed, when preventing or treating the above diseases and symptoms.

For the GPR160 gene inhibitor or receptor antagonist or a pharmaceutical composition thereof, the composition of the present invention may be used alone or in combination with other suitable anti-tumor agents through any suitable method. The administration methods that can be used include, but are not limited to: intracavitary injection, subcutaneous injection, intravenous injection, intramuscular injection, intradermal injection, local injection, and sustained release.

The effective amount of the GPR160 gene inhibitor or receptor antagonist according to the present invention may vary depending on the subject to be administered, the mode of administration, and the severity of the disease to be treated. The selection of the preferred effective amount can be determined by one of ordinary skill in the art based on a variety of factors, for example through clinical trials. The factors include but are not limited to: pharmacokinetic parameters of the GPR160 gene inhibitor or receptor antagonist, such as bioavailability, metabolism, half-life, etc; the severity of disease to be treated of the patient, patient weight, immune status, and route of administration.

In a specific embodiment, the method further comprises diagnosis, efficacy evaluation, and prognosis of the subject's disease or symptom. Any suitable method can be used for diagnosing and assessing related diseases or symptoms, therapeutic effects and prognosis. Diagnosis and prognosis can be performed based on the detection and/or identification of any or all of the substances in the body, for example, enzymes, antigens, antibodies, nucleic acids or other pathological and clinical markers, etc, and related symptoms.

Main Advantages of the Present Invention:

(1) Through a large number of screenings, a type of siRNA that has a significant inhibitory effect on GPR160 gene was obtained in the present invention;

(2) The siRNA of the present invention has a significant inhibitory effect on GPR160-positive tumors, particularly prostate cancer.

(3) A pharmaceutical composition comprising a GPR160 expression inhibitor or protein antagonist as a main component was provided in the present invention provides for the treatment of GPR160 high expression tumors, especially prostate cancer.

(4) A method for clinical diagnosis and drug screening using GPR160 as a target was provided in the present invention.

The present invention will be further illustrated below with references to the specific examples. It should be understood that these examples are only to illustrate the invention but not to limit the scope of the invention. The experimental methods with no specific conditions described in the following examples are generally performed under the conventional conditions, such as Sambrook, J., et al., Molecular Cloning Laboratory Guide (Translated by Huang Peitang, Beijing: Science Press, 2002), or according to the manufacture's instructions. Unless indicated otherwise, parts and percentage are calculated by weight. The experimental materials and reagents used in the following examples were obtained from commercial sources unless otherwise specified.

Example 1: Cell Culture

Human embryonic kidney epithelial cells 293T, prostate cancer cell lines PC-3, LNCaP, DU145, 22RV1, normal prostate epithelial cells RWPE-1 and Chinese hamster ovary cell CHO-K1 were purchased from ATCC. LNCaP and 22RV1 were cultured in high glucose RPMI1640 medium containing 10% FBS and 100 U/ml penicillin, and PC-3 and DU145 were cultured in normal RPMI1640 medium containing 10% FBS and 100 U/ml penicillin. The medium used for RWPE-1 was K-SF medium containing 50 µg/ml and 5 ng/ml epidermal growth factor. 293T was cultured in high glucose DMEM containing 10% FBS and 100 U/ml penicillin. CHO cells were cultured in F12 medium containing 10% FBS and 100 U/ml penicillin. All cells were cultured in a 37° C. incubator containing 5% $CO_2$.

Example 2: Detection of GPR160 Expression in Prostate Cancer Tissue and Prostate Cancer Cells by Quantitative RT-PCR (Probe Method)

The cDNA chips for prostate cancer tissue and normal prostate tissue were purchased from OriGene. The Taqman probe used for detecting was purchased from Invitrogen and the instrument, ViiA 7 Real-Time PCR Detection System (Applied Biosystems) was used. The total RNA of each cultured cell was extracted with Trizol reagent (Invitrogen), oligo-dT as primer, and reverse transcriptase was transcribed to generate cDNA. The reference gene is TATA box binding protein gene. The results are shown in FIG. 1, the expression level of GPR160 in prostate cancer tissues was significantly higher than that in normal prostate tissues (FIG. 1A); Whether in androgen-dependent (LNCaP and 22RV1) or hormone-independent (PC-3 and DU145) prostate cancer cells, the expression level of the endogenous GPR160 was significantly higher than that of normal prostate epithelial cells RWPE-1 (FIG. 1B).

Example 3: Detection of GPR160 Expression in Prostate Cancer Cells by Quantitative RT-PCR (SYBR Method)

The total RNA of each cultured cell was extracted with Trizol reagent (Invitrogen), Oligo-dT was used as primer, and reverse transcriptase was transcribed to generate cDNA. The template and primers were mixed with SYBR detection reagents (TaKaRa) and detected by 7300 Quantitative PCR instrument. The reference gene encodes the β-actin gene ACTB (NC 000007.14).

The target gene of the amplified sequence is shown in SEQ ID NO:1.

The primer sequences are listed as follows:

```
GPR160 gene:
Forword,
                                    SEQ ID NO.: 2
5'-TGCAGTCCGGAGACGAACG-3'

Reverse,
                                    SEQ ID NO.: 3
5'-GTAAGCTCGGAGACATTTGCG-3'

ACTB
Forward,
                                    SEQ ID NO.: 4
5'-GAGAAAATCTGGCACCACACC-3'

Reverse,
                                    SEQ ID NO.: 5
5'-TACCCCTCGTAGATGGGCAC-3'
```

Example 4: Inhibition of the Growth of Prostate Cancer Cells by GPR160-Interfering Small RNAs 4.1 Preparation of GPR160-Interfering Small RNA In order to continuously inhibit the expression of the intracellular GPR160 gene, the inventors used a lentivirus expression system. The lentivirus shRNA expression plasmid (Cat. No. TL312662) was purchased from OriGene, in which the target gene sequence targeted by the GPR160 siRNA is shown in SEQ ID NO: 1, and the sense strand sequence of the siRNA is shown in SEQ ID NO.: 6, SEQ ID NO: 7, SEQ ID NO.: 8, SEQ ID NO: 9, respectively. The sense strand sequence of the non-specific control siRNA is shown in SEQ ID NO: 10.

```
(ShGPR160-S6)
                                      SEQ ID NO.: 6
5'-TTGGTACAGGCTATCAGGATAACTTCCTA-3'

(ShGPR160-S7)
                                      SEQ ID NO.: 7
5'-TTCTATGTCAGCATTCAGAGTTACTGGCT-3'

(ShGPR160-S8)
                                      SEQ ID NO.: 8
5'-CCATCTACCAAAGCCTGAAGGCACAGAAT-3'

(ShGPR160-S9)
                                      SEQ ID NO.: 9
5'-CCATTTGTCAACTGGAAGTGCTGCTTCAT-3'

(ShGPR160-S10)
                                      SEQ ID NO.: 10
5'-GCACTACCAGAGCTAACTCAGATAGTACT-3'
```

The siRNA expression plasmid pGFP-C-shGPR160 and the control plasmid pGFP-C-Scramble were extracted with Qiagene plasmid extraction kit and mixed with the packaging plasmid, and then 293T cells that had been inoculated for 24 hours were transfected with MegaTran (OriGene), and the virus supernatant was collected after 72 hours. After centrifugation at 15000 rpm for 15 minutes to remove cell debris, a quarter volume of Lentivirus Concentration (Biomiga) was added for concentration, and was stored at −80° C. in aliquots. Viruses produced by transfection of pGFP-C-shGPR160 plasmid containing the sequences SEQ ID NO: 6 to SEQ ID NO: 9 were labeled as ShGPR160-S6, ShGPR160-S7, ShGPR160-S8, and ShGPR160-S9, respectively. The virus produced by transfection of the non-specific control plasmid was designated ShGPR160-S10.

Figure 2:
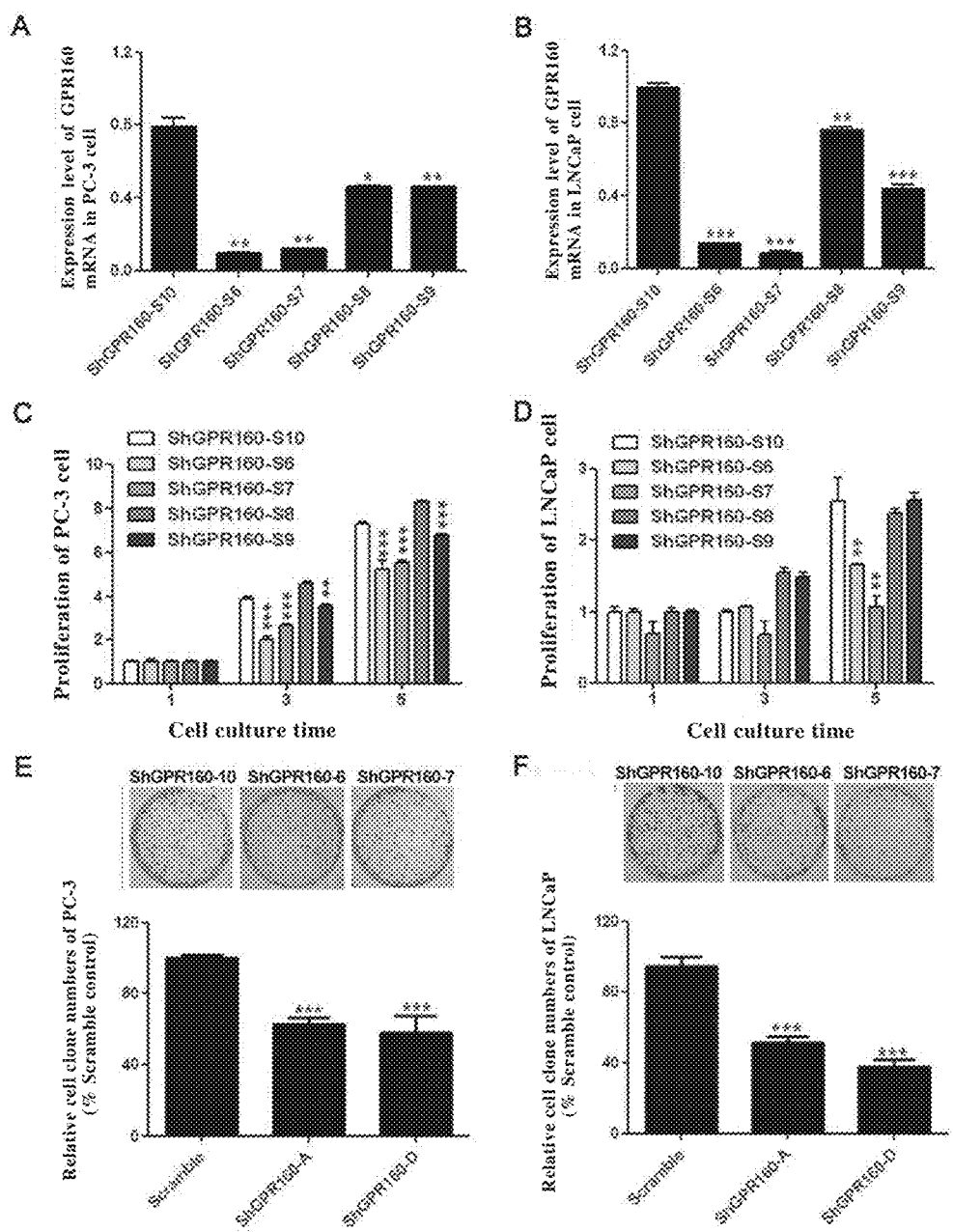
FIG. 2 shows the inhibitory effects of GPR small interference RNA on prostate cancer cells. A and B show the results of quantitative RT-PCR, wherein specific siRNA significantly reduces expression of GPR160 gene in PC-3 cells (A) and LNCaP cells (B); C and D: Specific siRNAs inhibit the proliferation of PC-3 cells (C) and LNCaP cells (D); E and F: Specific siRNAs inhibit the formation of clones of PC-3 cells (E) and LNCaP cells (F).

PC-3 and LNCaP cells were infected with the prepared lentiviruses at multiplicity of infection (MOI) of 40 and 10, respectively. After 72 hours, the total RNA of the infected cells was extracted, and the expression of GPR160 in the cells was detected by quantitative RT-PCR. The results showed that the inhibitory efficiency of ShGPR160-S6 in PC-3 and LNCaP was 87.8% and 86.2%, respectively, and the inhibitory efficiency of ShGPR160-S7 in two cells was 85.0% and 91.7%, respectively; the inhibitory efficiency of ShGPR160-S8 in PC-3 and LNCaP was 41.7% and 32.8%, respectively, and the inhibitory efficiency of ShGPR160-S9 in two cells was 41.8% and 56.2%, respectively, compared with the control virus ShGPR160-S10-treated group. The inhibitory effect of ShGPR160-S6 and ShGPR160-S7 on cell endogenous GPR160 expression was significantly better than that of ShGPR160-S8 and ShGPR160-S9 (FIGS. 2A and 2B).

A large number of siRNA molecules targeting GPR160 gene were screened by the inventors and it was found that siRNA molecules comprising the nucleotide sequence shown in SEQ ID NO.: 6 or SEQ ID NO.: 7 can significantly inhibit the GPR160 gene expression, the inhibitory activity of which is much better than that of other small interfering RNA molecules.

4.2 Effect of GPR160-Specific SiRNA on Growth of Prostate Cancer Cells

To examine the effect of GPR160-specific SiRNAs on proliferation of prostate cancer cells, PC-3 and LNCaP cells, after infected by virus for 48 hours, were plated in 96-well plates at a density of 5000/100/μl/well and 2500/100 μl/well, respectively, and cultured for 1, 3, and 5 days respectively, 10 μl/well of CCK-8 detection reagent (TaKaRa) was added 4 hours before the end of culture, and light absorption at 450 nm was detected at the end of incubation. The reference wavelength was 650 nm. The reading of Scramble group was set to 100%. The results are shown in FIGS. 2C and 2D. Both ShGPR160-S6 and ShGPR160-S7 significantly inhibited the proliferation of PC-3 and LNCaP cells; ShGPR160-S8 had no inhibitory effect on both cells; the effect of ShGPR160-S8 was obvious in PC-3, but had no significant effect on the growth of LNCaP.

Based on the above results, PC-3 and LNCaP cells were infected with ShGPR160-S6, ShGPR160-S7, and ShGPR160-S10 for 48 hours, and inoculated into 96-well plates at 1000/2 ml/well. After 12 to 20 days of continuous culture, the cells were stained with 0.1% crystal violet solution, dried, and the number of colonies per well counted. The group infected with ShGPR160-S10 virus was set as a 100% control. The results showed that the number of clones formed after infection with ShGPR160-S6 and ShGPR160-S7 was significantly less than that of the ShGPR160-S10 control group, whether in PC-3 or LNCaP cells (FIGS. 2E and 2F).

Thus, reducing the expression of endogenous GPR160 can inhibit the growth and colony formation of prostate cells.

4.3 Apoptosis of Prostate Cancer Cells Induced by GPR160 SiRNA

Figure 3:
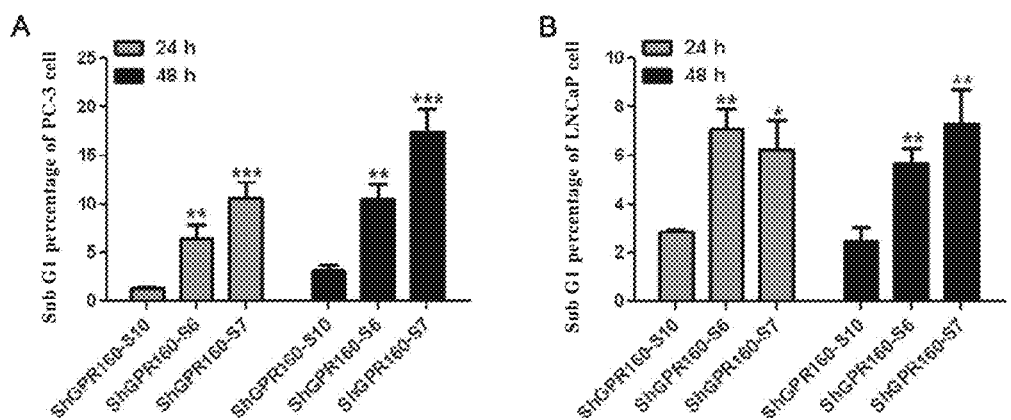
FIG. 3 shows GPR160-specific siRNAs significantly increased the ratio of DNA hypodiploid peaks in PC-3 cells (A) and LNCaP cells (B).

PC-3 and LNCaP cells, after infected by virus for 48 hours, were digested again with trypsin (Invitrogen), culture for another 48 hours, and collected at 1000 rpm×5 minutes, including cell debris in the culture broth. Cells were washed with 4° C. pre-cooled PBS, and then centrifuged again. The supernatant was discarded and cells were fixed with 70% alcohol pre-cooled at 4° C., and treated in 50 μg/ml PI solution and 100 μg/ml RNase A (Tiangen) at 37° C. for 30 minutes. The content of intracellular DNA was detected using Accuri C6 flow cytometer (BD Biosciences). Infection from Lentivirus encoding SiRNAs specific for GPR160 significantly increased sub-G 1 peaks of cellular DNA (FIG. 3), indicating the presence of apoptosis.

Figure 4:
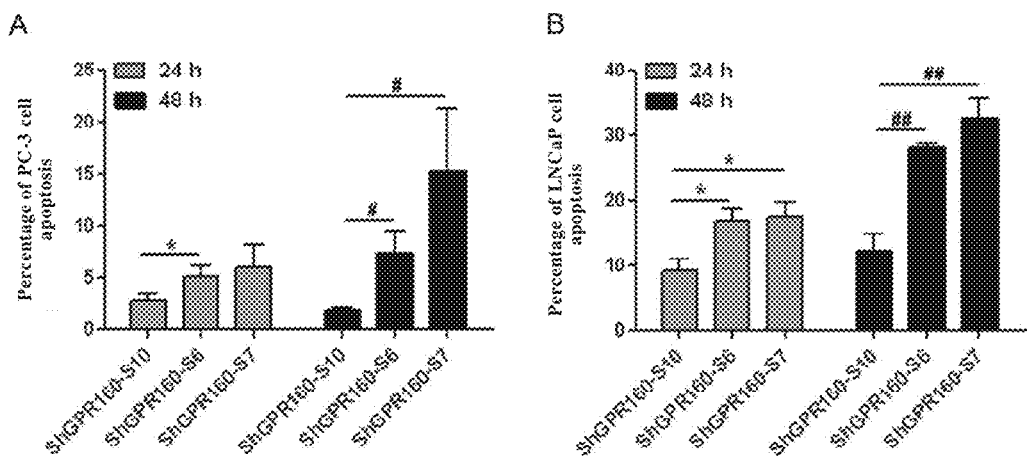
FIG. 4 shows GPR160-specific siRNA induces the apoptosis of prostate cancer cells. After being infected with lentivirus encoding GPR160 siRNA, PC-3 cells (A) and LNCaP cells (B) are double-stained with Annexin v and PI. The figure shows the proportion of cells stained positively by Annexin V. The ratio was significantly higher in GPR160 siRNA treated cells than that in control siRNA treated cells.

Apoptosis was further detected using APC labeled Annexin V and propidiumiodide (pI) and double-staining. Cells were harvested and collected into a 6-well plate after infecting for 48 hours. Cells were cultured for another 48 hours, collected, washed once with PBS, and re-suspended in 100 μL of 1× Annexin-binding buffer. 1 μl of PI solution (100 μl/ml) and 5 μl of APC-conjugated Annexin V solution were added, and cells were stained at room temperature for 15 minutes. Then 400 μL 1× Annexin-binding buffer was added to cells and the number of cells was detected by flow cytometry. Infection from Lentivirus encoding siRNAs specific for GPR160 significantly increased apoptosis of cells (FIG. 4).

Example 5: Screening of GPR160 Small Molecule Modulators

Figure 5:
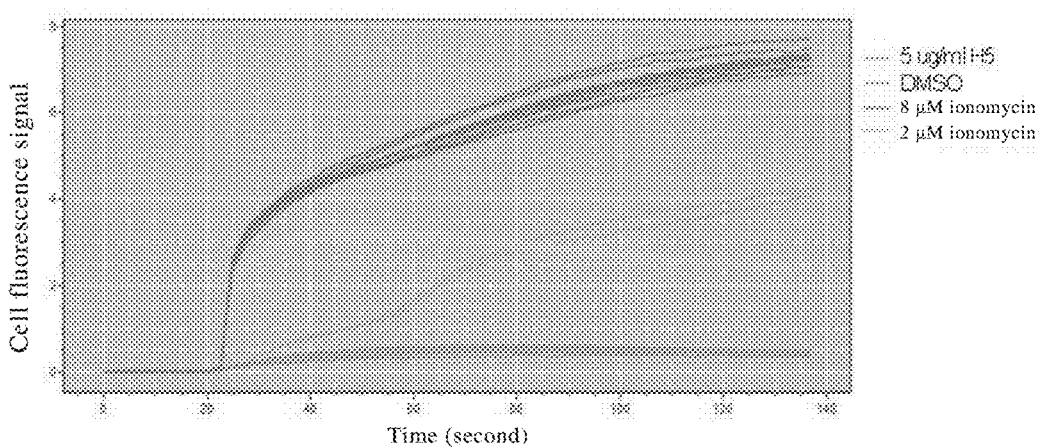
FIG. 5 shows screening of a small molecule agonist of GPR160 using a CHO cell line stably transfected with GPR160 and $G\alpha_{16}$. The green curve is the DMSO solvent control; the red curve shows the signal response induced by stimulation from 8 μM of Ionomycin (ionomycin), and the yellow curve is 2 μM of Ionomycin; and the gray curve is a signal response generated by 5 ul/ml of compound H5.

To screen small molecule antagonists of GPR160, the inventors intended to prepare a screening model to screen small molecule agonists. CHO cells were co-transfected with plasmids expressing GPR160 and $G_{\alpha16}$, and the stable clones were screened with 600 μg/ml neomycin and 200 μg/ml hygromycin. The expression of receptors on the cell surface was analyzed by immunofluorescence, and calcium flow reaction of the cells was identified with the calcium ionophore Ionomycin. Cell lines with a consistently high level of expression of GPR160 and good intracellular calcium flow reaction were screened and obtained for screening GPR160 small molecule modulators. The specific screening process is as follows:

CHO-$G_{\alpha16}$-GPR160 cells were seeded in 384-well cell culture plates at 5000/30 μl/well, and after incubating overnight, an equal volume of Calcium 5 detection reagent (Molecular Devices) was added to each well. After incubation at 37° C. for 45 minutes, cells were detected using a FLIPR fluorescence plate reader. The addition volume of the compound was 10 μl/well (20 μg/ml, 2% DMSO). The excitation wavelength was 485 nm and the emission wavelength was 525 nm. As shown in FIG. 5, the negative control was DMSO with a final concentration of 0.5%, and the positive controls were 8 μM (red) and 2 μM (yellow) ionomycin, respectively. The grey curve is the reaction signal of the representative active compound H5 (final concentration 5 μg/ml).

The above examples are for illustrative purposes only, and the scope of the present invention is not limited thereof. Modifications will be apparent to those skilled in the art and the invention is limited only by the scope of the appended claims.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

What we claim:

1. A dsRNA construct, wherein the dsRNA construct is double-stranded and the forward or reverse chain thereof has the structure shown in Formula I:

$$Seq_{Forward}\text{-}X\text{-}Seq_{Reverse} \qquad \text{Formula I}$$

wherein, $Seq_{forward}$ is a GPR160 gene fragment of SEQ ID NO: 6 or SEQ ID NO: 7;

$Seq_{reverse}$ is a nucleotide sequence that is substantially complementary to $Seq_{forward}$;

X is a spacer sequence located between Seq$_{forward}$ and Seq$_{reverse}$, and the spacer sequence is not complementary to Seq$_{forward}$ or Seq$_{reverse}$.

2. A dsRNA, wherein the dsRNA has the structure as shown in Formula II:

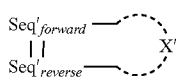

Formula II wherein,

Seq'$_{forward}$ is a RNA sequence corresponding to the GPR160 gene fragment sequence of SEQ ID NO: 6 or SEQ ID NO: 7;

Seq'$_{reverse}$ is a sequence that is substantially complementary to Seq'$_{forward}$;

X' is none, or a spacer sequence located between Seq'$_{forward}$ and Seq'$_{reverse}$, and the spacer sequence is not complementary to Seq'$_{forward}$ and Seq'$_{reverse}$;

ll represents a hydrogen bond formed between Seq'$_{forward}$ and Seq'$_{reverse}$.

3. A expression vector, wherein the expression vector comprises the dsRNA construct of claim 1.

4. A host cell, wherein the host cell comprises the expression vector of claim 3 or has a DNA sequence corresponding to the dsRNA construct of claim 1 incorporated into its chromosome.

5. A composition, wherein the composition contains an inhibitor inhibiting GPR160 gene expression by interfering with GPR160 gene fragment of SEQ ID NO: 6 or SEQ ID NO: 7; wherein the inhibitor includes: small interfering molecules or antisense nucleotides that specifically interfere with GPR160 gene expression.

6. The composition of claim 5, wherein the composition contains the dsRNA construct of claim 1 and/or the dsRNA of claim 2, and a pharmaceutically acceptable carrier.

7. The composition of claim 5, wherein the composition is a composition for inhibiting the expression of endogenous GPR160 gene in an animal.

8. A method for inhibiting GPR160 gene expression, comprising administering to a subject in need thereof an effective amount of the dsRNA construct of claim 1.

9. A method for preparing dsRNA, including steps of:
(i) preparing a construct expressing dsRNA, wherein the construct is double-stranded, and its sense or antisense strand contains the structure shown in Formula 1:

Seq$_{Forward}$-X-Seq$_{Reverse}$      Formula I wherein,

Seq$_{forward}$ is a GPR160 gene fragment of SEQ ID NO: 6 or SEQ ID NO: 7;

Seq$_{reverse}$ is a nucleotide sequence that is substantially complementary to Seq$_{forward}$;

X is a spacer sequence located between Seq$_{forward}$ and Seq$_{reverse}$, and the spacer sequence is not complementary to Seq$_{forward}$ or Seq$_{reverse}$;

(ii) transferring the construct in step (i) into a host cell, thereby forming dsDNA as shown in Formula II in the host cell through expression,

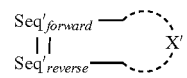

Formula II wherein,

Seq'$_{forward}$ is a RNA sequence or sequence fragment corresponding to Seq$_{forward}$;

Seq'$_{reverse}$ is a sequence that is substantially complementary to Seq'$_{forward}$;

X' is none, or a spacer sequence located between Seq'$_{forward}$ and Seq'$_{reverse}$, and the spacer sequence is not complementary to Seq'$_{forward}$ or Seq'$_{reverse}$;

ll represents a hydrogen bond formed between Seq'$_{forward}$ and Seq'$_{reverse}$.

10. The method of claim 9, wherein the spacer sequence X is 1-100 bp in length, preferably 4-10 bp.

11. The method of claim 10, wherein the GPR160 gene or GPR160 gene fragment is derived from mammal, preferably from human.

12. A method for inhibiting GPR160 gene expression, comprising contacting cells expressing GPR160 with an effective amount of a nucleic acid comprising the nucleotide sequence of SEQ ID NO: 6 or SEQ ID NO: 7.

13. The method of claim 12, wherein the nucleic acid is an siRNA.

14. The method of claim 8, wherein the subject is a human patient having prostate cancer.

* * * * *

SEQUENCE LISTING

```
<160> NUMBER OF SEQ ID NOS: 12

<210> SEQ ID NO 1
<211> LENGTH: 2021
<212> TYPE: DNA
<213> ORGANISM: Homo sapiens

<400> SEQUENCE: 1
ggcccggacg ggacgtgcgc gctcaaaggt tgcccgtctc tgacgcccgc atttcctggt      60
ctggagccgg ctgagccaca gcagggtcgc cgcggggtcc cggggccgtg ctcccctgcc     120
cctcccggga gcgcgcgggg cggggcgggg cggggcggga ccaggcgggc gagctgggcc     180
ctcgcccctc cctcgggcgg tcacctgggc acgggcgctg caggtgtcgg ggcctcaacc     240
ttgcggagcc gacagccatc gatcctcggg tggcctcgag gtggtggcag ggccgccccc     300
tgcagtccgg agacgaacgc acggaccggg cctccggagg caggttcggc tggaaggaac     360
cgctctcgct tcgtcctaca cttgcgcaaa tgtctccgag cttactcaca tagcatattg     420
gtatatcaaa atgaaatgca aggaaccaaa aataacataa ttgaaggcag taaaagtgaa     480
attaaatagg aagatcatca gtcaaggaag acccactgga gaggacagaa aatgaagcag     540
tgttttatca tgtgtatttc agcaggtctt cttgaaattt aactaaaaat atgactgctc     600
tctcttcaga gaactgctct tttcagtacc agttacgtca aacaaaccag cccctagatg     660
ttaactatct gctattcttg atcatacttg ggaaaatatt attaaatatc cttacactag     720
gaatgagaag aaaaaacacc tgtcaaaatt ttatggaata tttttgcatt tcactagcat     780
tcgttgatct tttacttttg gtaaacattt ccattatatt gtatttcagg gattttgtac     840
ttttaagcat taggttcact aaataccaca tctgcctatt tactcaaatt atttccttta     900
cttatggctt tttgcattat ccagttttcc tgacagcttg tatagattat tgcctgaatt     960
tctctaaaac aaccaagctt tcatttaagt gtcaaaaatt attttatttc tttacagtaa    1020
ttttaatttg gatttcagtc cttgcttatg tttttgggaga cccagccatc taccaaagcc    1080
tgaaggcaca gaatgcttat tctcgtcact gtcctttcta tgtcagcatt cagagttact    1140
ggctgtcatt tttcatggtg atgattttat ttgtagcttt cataacctgt tgggaagaag    1200
ttactacttt ggtacaggct atcaggataa cttcctatat gaatgaaact atcttatatt    1260
ttcctttttc atcccactcc agttatactg tgagatctaa aaaaatattc ttatccaagc    1320
tcattgtctg ttttctcagt acctggttac catttgtact acttcaggta atcattgttt    1380
tacttaaagt tcagattcca gcatatattg agatgaatat tccctggtta tactttgtca    1440
```

-continued

| | |
|---|---|
| atagttttct cattgctaca gtgtattggt ttaattgtca caagcttaat ttaaaagaca | 1500 |
| ttggattacc tttggatcca tttgtcaact ggaagtgctg cttcattcca cttacaattc | 1560 |
| ctaatcttga gcaaattgaa aagcctatat caataatgat ttgttaatat tattaattaa | 1620 |
| aagttacagc tgtcataaga tcataatttt atgaacagaa agaactcagg acatattaaa | 1680 |
| aaataaactg aactaaaaca acttttgccc cctgactgat agcatttcag aatgtgtctt | 1740 |
| ttgaagggct atgataccag ttattaaata gtgttttatt ttaaaaacaa ataattcca | 1800 |
| agaagttttt atagttattc agggacacta tattacaaat attactttgt tattaacaca | 1860 |
| aaaagtgata agagttaaca tttggctata ctgatgtttg tgttactcaa aaaaactact | 1920 |
| ggatgcaaac tgttatgtaa atctgagatt tcactgacaa ctttaagata tcaacctaaa | 1980 |
| cattttattt aaatgttcaa atgaaagcaa gaaaaaaaaa a | 2021 |

```
<210> SEQ ID NO 2
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 2
```

| | |
|---|---|
| tgcagtccgg agacgaacg | 19 |

```
<210> SEQ ID NO 3
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 3
```

| | |
|---|---|
| gtaagctcgg agacatttgc g | 21 |

```
<210> SEQ ID NO 4
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 4
```

| | |
|---|---|
| gagaaaatct ggcaccacac c | 21 |

```
<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
```

| | |
|---|---|
| taccectcgt agatgggcac | 20 |

```
<210> SEQ ID NO 6
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 6
```

| | |
|---|---|
| ttggtacagg ctatcaggat aacttccta | 29 |

```
<210> SEQ ID NO 7
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 7
ttctatgtca gcattcagag ttactggct                                29

<210> SEQ ID NO 8
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 8
ccatctacca aagcctgaag gcacagaat                                29

<210> SEQ ID NO 9
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 9
ccatttgtca actggaagtg ctgcttcat                                29

<210> SEQ ID NO 10
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 10
gcactaccag agctaactca gatagtact                                29

<210> SEQ ID NO 11
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 11
taggaagtta tcctgatagc ctgtaccaa                                29

<210> SEQ ID NO 12
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 12
agccagtaac tctgaatgct gacatagaa                                29
```